United States Patent [19]
Skerra et al.

[11] Patent Number: 6,103,493
[45] Date of Patent: Aug. 15, 2000

[54] STREPTAVIDIN MUTEINS

[75] Inventors: Arne Skerra, Darmstadt; Selma Voss, Ingelheim, both of Germany

[73] Assignee: Institut Fur Bioanalytic, Gottingen, Germany

[21] Appl. No.: 08/948,097

[22] Filed: Oct. 9, 1997

[51] Int. Cl.[7] .......................... C12P 21/06; C07H 17/00; C07K 14/00
[52] U.S. Cl. ...................... 435/69.1; 435/7.1; 435/320.1; 435/325; 435/252.3; 536/23.1; 530/300; 530/320; 530/330; 530/350
[58] Field of Search ..................................... 530/350, 300, 530/328, 330; 435/69.1, 320.1, 325, 252.3, 7.1; 536/23.1

[56] References Cited

PUBLICATIONS

Chilkoti et al. 1995 Proc. Natl. Acad. Sci. 92: 1754–1758.
Reznik et al. 1996 Nature Biotechnology 14: 1007–1011.
Reznik et al. Nov. 10 1998 Proc. Natl'l. Acad. Sci. 95: 13525–13530.
Sano et al. Jun. 10, 1997, Proc. Natl. Acad. Sci. 94:6153–6158.
Voss et al. Aug., 1997. Protein Eng. 10(8): 975–982.

*Primary Examiner*—Karen Cochrane Carlson
*Attorney, Agent, or Firm*—Fulbright & Jaworski, LLP

[57] ABSTRACT

The invention concerns a polypeptide selected from muteins of streptavidin which is characterized in that it (a) contains at least one mutation in the region of the amino acid positions 44 to 53 with reference to wild type-(wt)-streptavidin and (b) has a higher binding affinity than wt-streptavidin for peptide ligands comprising the amino acid sequence Trp-X-His-Pro-Gln-Phe-Y-Z in which X represents an arbitrary amino acid and Y and Z either both denote Gly or Y denotes Glu and Z denotes Arg or Lys. In addition nucleic acids coding for the polypeptide, a vector containing this nucleic acid, a cell transfected with the vector as well as the use of a polypeptide in a method for the isolation, purification or determination of proteins are disclosed. Yet a further subject matter is a reagent kit containing the polypeptide.

30 Claims, 3 Drawing Sheets

STREPTAVIDIN MUTEINS

FIELD OF THE INVENTION

The present invention concerns streptavidin muteins, a process for the production of such proteins by means of recombinant DNA technology as well as the use of these streptavidin muteins for the isolation, purification and determination of biological substances, in particular of other recombinant proteins.

BACKGROUND AND PRIOR ART

Nowadays the biotin/streptavidin system is a generally known binding system in molecular biology the importance of which has increased considerably in recent years and which is used in various fields of application. In doing so one utilizes the specific affinity between biotin and streptavidin which, together with an affinity constant of the order of 1013, is one of the most stable known non-covalent interactions.

Important conventional applications are for diverse separation and detection methods usually using biotinylated enzymes or/and antibodies in various variations. Examples are for example ELISA, Western blot etc. A prerequisite for such methods is that the reagent or enzyme used in a biotinylated form in the method must firstly be obtainable in a pure form in order to be able to carry out the biotinylation which takes place in a chemical reaction.

However, for certain applications a biotinylation is not possible or at least not in a simple manner such as for example when detecting and purifying recombinantly produced proteins which have previously not yet been isolated. Therefore in the past methods for modifying the biotin/streptavidin system have been sought in order to extend its range of application.

A successful approach has been to produce peptide ligands which also have a specific binding affinity for streptavidin. Suitable peptide ligands and corresponding fusion proteins are disclosed in DE-OS 42 37 113. The advantage of these peptide ligands compared to biotin is essentially that their coding sequence is linked at the DNA level with the gene of a desired protein and can subsequently be coexpressed together with that of the protein by which means a recombinant protein labelled with the peptide ligand, i.e. fused thereto, is formed. Due to the small size of the peptide ligands and the fact that they can be attached to the N- or C-terminus of the desired protein, i.e. in areas which often are not of major importance for the structure and biochemical function of the protein, it is generally also not necessary to again cleave off the peptide ligand after its isolation and before using the protein for other purposes so that this also results in a more economical process. Indeed no case is yet known in which a cleavage would have been necessary. If nevertheless cleavage should be necessary, this can be accomplished by inserting a protease cleavage site between the binding peptide and protein sequence.

Such peptide ligands which are suitable are described in detail for example in Schmidt and Skerra, Protein Eng. 6 (1993), 109–122 and J. Chromatogr. A 676 (1994), 337–345 as well as in Schmidt et al., J. Mol. Biol. 255 (1996), 753–766.

Advantages of the streptavidin peptide ligand system are that the purification of recombinant proteins becomes possible at all and that this purification can be achieved for example by affinity chromatography under very mild elution conditions since the bound peptide ligand as part of the recombinant protein is displaced competitively by biotin or derivatives thereof. In addition the peptide ligand enables the recombinant protein to be for example detected by Western blot, ELISA or by immune microscopy using suitable streptavidin conjugates.

A disadvantage of this system has previously been its relatively low affinity. An affinity constant of $2.7 \times 10^4$ $M^{-1}$ has been determined by means of isothermal titration calorimetry for the complex between streptavidin and the peptide ligand referred to as strep-tag (Ala Trp Arg His Pro Gln Phe Gly Gly (SEQ ID NO: 1)). Although there were indications that the binding could be somewhat stronger for a fusion protein containing the peptide ligand, it is desirable to have a system with a fundamentally improved affinity.

Hence the object of the invention was to optimize the streptavidin/peptide ligand system with regard to binding strength.

After initial experiments had been carried out to further optimize the sequence of the peptide ligand, it had to be assumed that the peptide ligand according to DE-OS-4237113 already apparently represented an optimum and thus this approach was less promising.

Once the crystal structure of the streptavidin/peptide ligand complex was available in high resolution, a better understanding was gained of the molecular interactions and the structural characteristics (Schmidt et al. (1996), supra) but no clear information could be obtained from these structural data on whether and in which manner a modification of the peptide sequence or of streptavidin could be carried out in a rational manner to improve the affinity and hence to achieve the initial objective.

In an evolutionary research approach it has now been surprisingly found that the binding affinity for the streptavidin/peptide ligand system can be improved by mutation in the region of the amino acid positions 44 to 53 of streptavidin.

SUMMARY OF THE INVENTION

Thus a subject matter of the present invention is a polypeptide selected from muteins of streptavidin which is characterized in that it (a) contains at least one mutation in particular an amino acid substitution in the region of the amino acid positions 44 to 53 with reference to the amino acid sequence of wild type-(wt)-streptavidin (nomenclature according to Argarana et al., Nucleic Acids Res. 14 (1986), 1871–1882) and (b) has a higher binding affinity than wt-streptavidin for peptide ligands comprising the amino acid sequence Trp-Xaa-His-Pro-Gln-Phe-Xaa-Xaa (SEQ ID NO: 16) in which X represents an arbitrary amino acid and Y and Z either both denote Gly or Y denotes Glu and Z denotes Arg or Lys.

The streptavidin muteins of the present invention can correspond to the amino acid sequence of wt-streptavidin outside of the region of the amino acid positions 44 to 53. On the other hand the amino acid sequence of the muteins according to the invention can also be different to the wt-streptavidin sequence outside the region of the amino acids 44 to 53. Such variants of th e streptavidin sequence include naturally occurring as well as artificially produced variants and the modifications are understood as substitutions, insertions, deletions of amino acid residues as well as N- or/ and C-terminal additions.

The term "higher binding affinity" refers within the sense of the present application to a complex composed of a streptavidin mutein according to the invention and a peptide ligand according to DE-OS-4237113 and can be determined by standard methods such as ELISA, fluorescence titration or titration calorimetry. The binding affinity determined in this manner is specified by parameters such as affinity and dissociation constants or thermodynamic parameters. The increase of the binding affinity which is obtained with a streptavidin mutein modified according to the invention within the region of the amino acid positions 44 to 53 compared to the corresponding unmodified streptavidin is in general at least a factor of 5, preferably at least a factor of 10 and more preferably at least a factor of 20. Preferred streptavidin muteins according to the invention comprise at least one mutation in the region of the amino acid positions 44 to 47.

Preferred streptavidin muteins according to the invention are derived from streptavidin variants which are shortened at the N- or/and the C-terminus. The minimal streptavidins which are N- and C-terminally shortened known from the state of the art are particularly preferred. A preferred polypeptide according to the present invention comprises outside of the mutagenized region the amino acid sequence of a minimal streptavidin which begins N-terminally in the region of the amino acid positions 10 to 16 and terminates C-terminally in the region of the amino acid positions 133 to 142. The polypeptide particularly preferably corresponds to a minimal streptavidin outside of the mutation region which comprises an amino acid sequence from position $Ala^{13}$ to $Ser^{139}$ and optionally has an N-terminal methionine residue. In this application the numbering of amino acid positions refers throughout to the numbering of wt-streptavidin (Argarana et al., Nucleic Acids Res. 14 (1986), 1871–1882).

Streptavidin muteins according to the invention that are especially preferred are characterized in that at position 44 Glu is replaced by a hydrophobic aliphatic amino acid e.g. Val, Ala, Ile or Leu, at position 45 an arbitrary amino acid is present, at position 46 an aliphatic amino acid and preferably a hydrophobic aliphatic amino acid is present or/and at position 47 Val is replaced by a basic amino acid e.g. Arg or Lys and in particular Arg. Streptavidin muteins in which the aliphatic amino acid at position 46 is Ala i.e. there is no substitution at position 46, or/and in which the basic amino acid at position 47 is Arg or/and in which the hydrophobic aliphatic amino acid at position 44 is Val or Ile have a particularly high affinity for the peptide ligand with the sequence WSHPQFEK (strep-tag II) described by Schmidt et al., Supra.

Specific examples of streptavidin muteins according to the invention have the sequences $Val^{44}$-$Thr^{45}$-$Ala^{46}$-$Arg^{47}$ (SEQ ID NO: 6) or $Ile^{44}$-$Gly^{45}$-$Ala^{46}$-$Arg^{47}$ (SEQ ID NO: 8) in the region of the amino acid positions 44 to 47.

For practical considerations it is desirable to have a further ligand which, due to a higher binding affinity or/and when present at higher concentrations, can detach the binding of the previously defined peptide ligands (according to DE-OS-4237113) from the streptavidin mutein according to the invention. In this manner it is possible to release bound peptide ligands or proteins to which a peptide ligand is fused under very mild elution conditions. Hence under this aspect the present invention concerns those streptavidin muteins according to the invention whose binding affinity for peptide ligands is such that they can be competitively eluted by other streptavidin ligands e.g. biotin, iminobiotin, lipoic acid, desthiobiotin, diaminobiotin, HABA (hydroxyazobenzene-benzoic acid) or/and dimethyl-HABA. The use of coloured substances such as HABA has the advantage that the elution can be checked visually.

However, irrespective of this, the binding affinity of the streptavidin mutein for peptide ligands is, as defined above, higher than that of the underlying wt-streptavidin. The binding affinity expressed as an affinity constant is thus greater than $2.7 \times 10^4$ $M^{-1}$ with reference to the peptide ligand Ala Trp Arg His Pro Gln Phe Gly Gly (also referred to as strep-tag in the following) shown in SEQ ID NO:1 and greater than $1.4 \times 10^4$ $M^{-1}$ with reference to the peptide ligand Trp Ser His Pro Gln Phe Glu Lys (also referred to as strep-tag II in the following) shown in SEQ ID NO:2 i.e. greater than the published values for the complex formation of the respective peptide ligands with wt-streptavidin (within the limits of error). In general the affinity constant for the strep-tag II is at least a factor of 10, preferably a factor of 10 to 200 higher than the respective values for wt-streptavidin.

It may be preferable for certain detection methods to use the streptavidin muteins of the present invention in a labelled form. Accordingly a further subject matter of this invention is a polypeptide according to the invention which is characterized in that it carries at least one label. Suitable labelling groups are known to a person skilled in the art and comprise the usual radiolabels, fluorescent labels, luminescent labels and chromophore labels as well as substances and enzymes which generate a substrate that can be determined in a chemical or enzymatic reaction. In this connection all labels known for wt-streptavidin can also be coupled to the streptavidin muteins according to the invention.

A further aspect of the present invention concerns a nucleic acid which comprises a sequence coding for the streptavidin. Such a nucleic acid is optionally operatively linked to a sequence coding for a signal peptide and, in a particular embodiment, the sequence coding for the signal peptide is the sequence for the OmpA signal peptide. Moreover it is also possible to use other signal peptides and this may even be preferable especially depending on the expression system or host cell used. A large number of such signal peptides are known in the state of the art and will not be elucidated in detail here. However, cytoplasmic expression is preferred i.e. with a start methionine instead of the signal sequence (cf. Schmidt and Skerra (1994), supra).

A further aspect of the present invention concerns a vector which contains at least one copy of an aforementioned nucleic acid in an operatively functional environment. An operatively functional environment is understood as those elements which enable, favour, facilitate or/and increase the expression, i.e. transcription or/and a subsequent processing, of the mRNA. Examples of such elements are promoters, enhancers, transcription initiation sites and termination sites, translation initiation sites, polyA-sites etc.

The vector is selected depending on the intended expression system and for this single copy plasmids, multi-copy plasmids as well as vehicles which facilitate an integration of the nucleic acid into the host genome come into consideration. A large number of suitable vectors are known from the state of the art and will not be described in detail here. They optionally contain standard elements used for vectors such as resistances, selection markers or/and elements which for example enable an amplification of the nucleic acid or the induction of expression.

A further aspect of the present invention concerns a cell which is transformed or transfected with such a vector which carries as an insert at least one copy of a nucleic acid sequence coding for a streptavidin mutein according to the invention. The selection of the cell is not particularly critical and in general it is possible to use any cells that are suitable for such purposes. Prokaryotic as well as eukaryotic cells and yeasts come into consideration. For practical reasons prokaryotic cells are generally preferred and in particular *E. coli* for the expression of an unglycosylated protein as in the present case.

Yet a further aspect of the present invention concerns a process for the production of a streptavidin mutein according to the invention which is characterized by the following steps:

(a) transforming a suitable host cell with a vector which contains a nucleic acid coding for the streptavidin mutein, (b) culturing the host cell under conditions in which an expression of the streptavidin mutein takes place, (c) isolating the polypeptide.

With respect to the production process it must be noted that the streptavidin muteins according to the invention may have a toxic effect due to their ability to bind to endogeneous cell biotin. Hence when culturing the host cell the conditions should be selected such that the expression product that forms is either transported from the inside of the host cell used for example into the periplasma or into the culture medium by means of a suitable signal sequence or it aggregates inside the cell in the form of insoluble inclusion bodies. In the former case the streptavidin mutein according to the invention can be isolated from the periplasmic cell fraction or the cell supernatant whereas in the latter case step (c) of the process according to the invention comprises the lysis of host cells, the isolation of the streptavidin mutein in the form of inclusion bodies and the renaturation of the streptavidin mutein. In this case *E. coli* is preferred as the host cell.

The practical applications for the streptavidin muteins or the streptavidin mutein/peptide ligand system according to the invention are essentially the same as those for conventional streptavidin/biotin or streptavidin/peptide ligand systems. There are advantages especially in situations in which a higher binding strength is desired than that between native streptavidin and peptide ligand or in situations in which it is not possible to biotinylate a substrate of interest or is less easy than the corresponding linkage to a peptide ligand.

The advantages over the conventional streptavidin/biotin system apply in particular to affinity chromatography and in purification, isolation or determination methods for recombinant proteins. Accordingly the invention also concerns the use of a streptavidin mutein according to the invention in a method for the isolation, purification or detection of a protein that is fused with a peptide sequence of the formula Trp-Xaa-His-Pro-Gln-Phe-Xaa-Xaa (SEQ ID NO: 16) in which X represents an arbitrary amino acid and Y and Z either both denote Gly or Y denotes Glu and Z denotes Arg or Lys wherein a liquid containing the protein to be isolated or purified is contacted with the optionally immobilized streptavidin mutein under suitable conditions in order to bind the peptide sequence to the streptavidin mutein, the resulting complex is separated from the liquid and the protein is released from the complex or detected. The peptide sequence is particularly preferably selected in the form of strep-tag or strep-tag II. The peptide sequence is preferably fused to the N- or/and C-terminus of the protein. The streptavidin mutein can be bound to a solid phase or can be capable of binding to it.

An advantage of utilizing the streptavidin mutein/peptide ligand system according to the invention in an isolation or purification method is that very mild conditions can be used to elute the fusion protein carrying the peptide ligand. Hence it is possible to incubate a solid phase coupled to the streptavidin mutein, such as for example an affinity chromatography column to which the fusion protein has been adsorbed, with an adequate concentration of a ligand selected from biotin and derivatives thereof in order to release the fusion protein from the complex. In this connection the use of desthiobiotin has proven to be particularly advantageous.

The streptavidin muteins according to the invention can be used in detection methods in an essentially similar manner to the corresponding methods that are known for conventional streptavidin. A further application is the qualitative or quantitative determination of a protein which is fused with a peptide sequence of the formula Trp-Xaa-His-Pro-Gln-Phe-Xaa-Xaa (SEQ ID NO: 16) in which X represents an arbitrary amino acid and Y and Z either both denote Gly or Y denotes Glu and Z denotes Arg or Lys, wherein the protein to be determined is contacted under suitable conditions with a labelled streptavidin mutein in order to bind the peptide sequence to the streptavidin mutein and the label is determined. Such a determination method can for example be carried out qualitatively to detect proteins in Western blots or quantitatively as an ELISA. Suitable labels are all known radioactive and non-radio-active labelling groups e.g. luminescent groups, enzymes, metals, metal complexes etc. The streptavidin can be directly labelled e.g. by covalent coupling. However, indirect labels such as labelled anti-streptavidin antibodies or biotinylated enzymes etc. can also be used.

A further subject matter of the invention is the use of the streptavidin muteins according to the invention to immobilize a protein which is fused with a peptide sequence Trp-Xaa-His-Pro-Gln-Phe-Xaa-Xaa (SEQ ID NO: 16) in which X represents an arbitrary amino acid and Y and Z either both denote Gly or Y denotes Glu and Z denotes Arg or Lys. This immobilization is preferably carried out on solid phases coated with streptavidin muteins such as microtitre plates, microbeads made of organic or paramagnetic materials or sensor chips.

In addition it is of course also possible to use the streptavidin muteins according to the invention in a conventional streptavidin/biotin (derivative) system. In other words this means the use of the streptavidin muteins according to the invention to determine or isolate substances which carry a group capable of binding to streptavidin. If only a part of the wt-streptavidin is replaced by the streptavidin muteins according to the invention, particular effects can be achieved in this connection via the formation of mixed tetramers.

Yet a further aspect of the invention also concerns a reagent kit which contains a streptavidin mutein according to the invention and optionally standard buffer and auxiliary substances and additives. Such a reagent kit is in particular intended to be used in one of the isolation, purification or determination methods described above. However, the kit is also suitable for other methods in which the conventional streptavidin/biotin system is used e.g. for nucleic acid hybridization assays or immunoassays. The reagent kit can contain the streptavidin mutein according to the invention in a solid phase-bound or/and labelled form.

The invention is further elucidated by the following examples and the attached figures in which.

BRIEF DESCRIPTION OF THE FIGURES

DETAILED DESCRIPTION OF PREFERRED EMBODIMENTS

Figure 1:
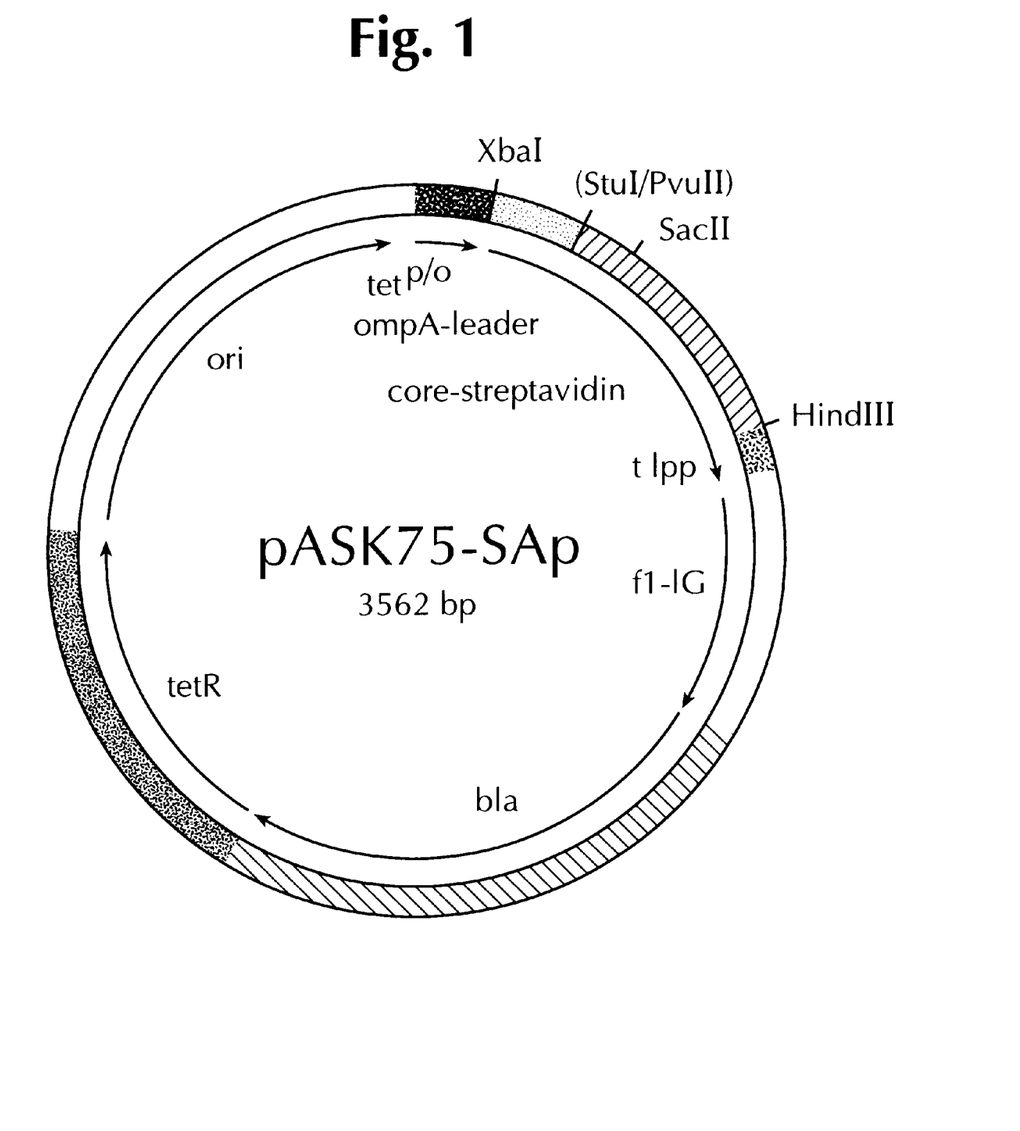
FIG. 1 shows a schematic drawing of the vector pASK75-SAp.

FIG. 1 shows the expression vector pASK75-SAp which contains a sequence coding for a minimal streptavidin (Ala$^{13}$ to Ser$^{139}$), a sequence coding for the OmpA signal peptide as well as the tetracyclin promoter/operator (tet$^{P/O}$) for transcription regulation.

Other labelled regions of the vector are the intergenic region of the filamentous phage f1 (f1-IG), the origin of replication (ori), the β-lactamase gene (bla) for ampicillin resistance, the tetracyclin repressor gene (tetR) and the lipoprotein transcription terminator ($t_{lpp}$).

The hybrid structural gene containing the coding sequences for the signal peptide and minimal streptavidin begins at the XbaI site and extends downstream to the HindIII site. The junction between the signal sequence and streptavidin is at the StuI/PvuII site. The SacII site which was used to insert the mutated streptavidin gene sequences is also shown.

Figure 2:
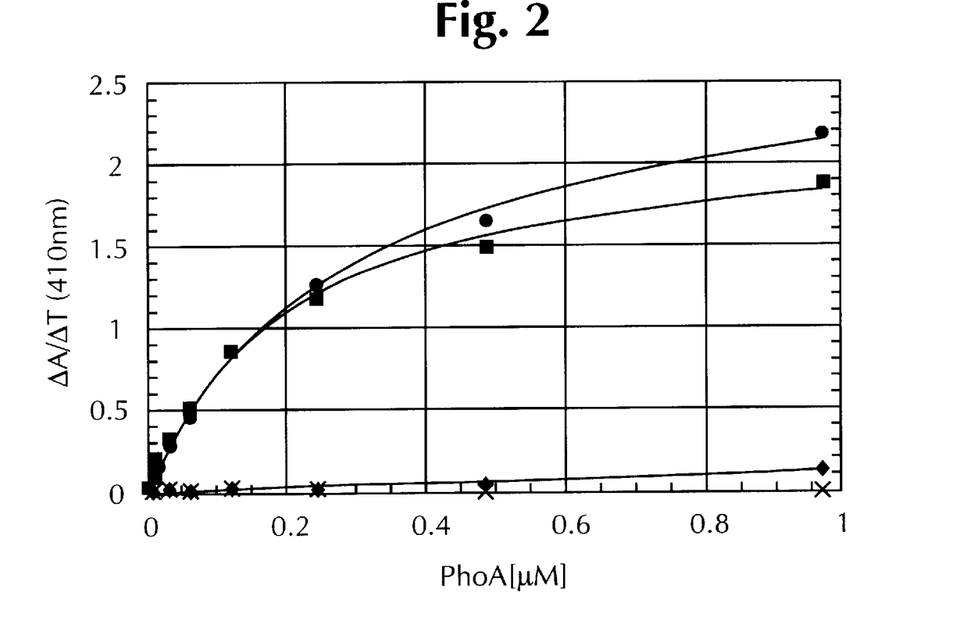
FIG. 2 is a graph which shows the binding affinity of recombinant wt-streptavidin compared to streptavidin muteins according to the invention in an ELISA.

FIG. 2 shows the improved affinity of the streptavidin muteins according to the invention for the peptide ligand strep-tag II in an ELISA. For this rows of an ELISA plate were each coated with equivalent concentrations of a recombinant wt-streptavidin (rhombus), the mutein "1" (circle) or "2" (square) or only saturated with BSA (cross). After saturating and washing the wells were incubated with a purified fusion protein consisting of bacterial alkaline phosphatase (PhoA) and strep-tag II at the concentrations shown in the graph. After washing to remove unbound protein, the activity of the bound PhoA-strep-tagII fusion protein was measured in the presence of p-nitrophenyl phosphate. The data were fitted by non-linear regression by the least squared error method. The following $K_d$ values were obtained: 0.21 µM for mutein "1"; 0.30 µM for mutein "2"; 18 µM for recombinant wt-streptavidin.

Figure 3:
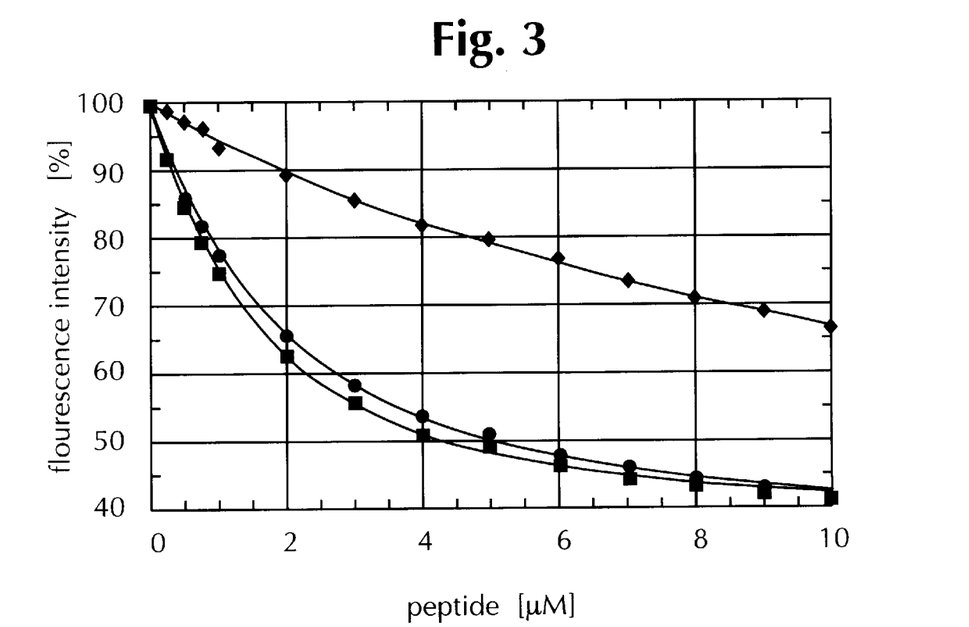
FIG. 3 shows the binding affinity of recombinant wt-streptavidin compared to a streptavidin mutein according to the invention in a fluorescence titration and FIG. 4 shows the purification of a strep-tag fusion protein using a streptavidin mutein by affinity chromatography.

FIG. 3 is a graph which shows the binding affinity of recombinant wt-streptavidin compared to streptavidin muteins according to the invention in a fluorescence titration.

A solution of wt-streptavidin (rhombus), the mutein "1" (circle) or "2" (square) was titrated with a solution of the synthesized strep-tag II peptide which was derivatized N-terminally with anthranilic acid and the fluorescence of the tryptophan and tyrosine residues was measured (excitation at 280 nm; emission at 340 nm). The experimental conditions are described in example 6. A $K_D$ value for the peptide complex of 13.0±1.3 µM for wt-streptavidin was determined by non-linear regression of the data points according to the theory of simple complex formation whereas the mutants "1" and "2" had $K_D$ values of 1.37±0.08 µM and 1.02±0.04 µM respectively.

Figure 4:
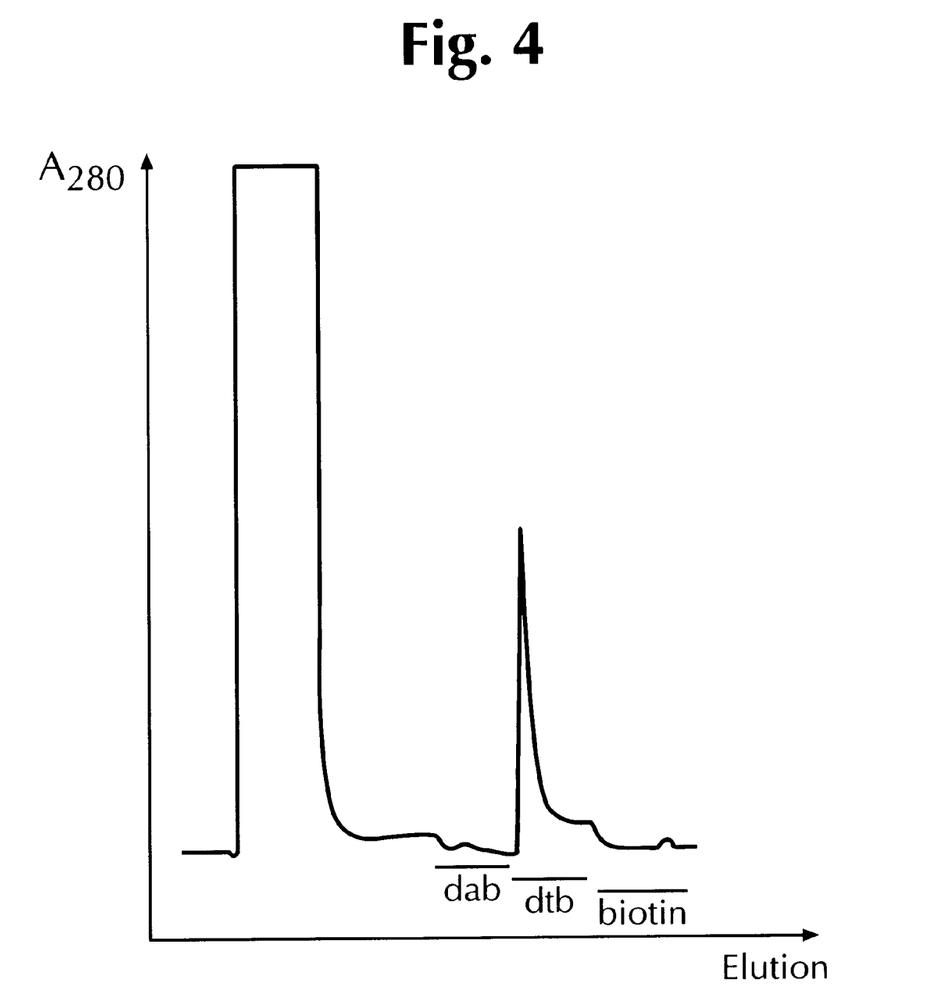

FIG. 4 shows the purification of the fusion protein composed of bacterial alkaline phosphatase and strep-tag II by affinity chromatography using the immobilized streptavidin mutein "1" according to the invention.

FIG. 4 shows the elution profile (based on the absorbance of the eluate at 280 nm) when purifying the fusion protein composed of bacterial alkaline phosphatase and strep-tag II by affinity chromatography from the bacterial periplasmic cell extract using the immobilized streptavidin mutein "1". The experimental conditions are described in example 4. After removing the host proteins by washing with chromatography buffer, it was eluted successively with solutions of diamino-biotin (dab), desthiobiotin (dtb) and biotin. The bound fusion protein was almost quantitatively eluted in the presence of desthiobiotin. Subsequent analysis by SDS polyacrylamide gel electrophoresis showed an almost complete purity of the protein isolated in this manner.

The invention is further elucidated by the following sequence protocol:

SEQ ID NO. 1: shows the amino acid sequence of the peptide ligand strep-tag,

SEQ ID NO. 2: shows the amino acid sequence of the peptide ligand strep-tag II,

SEQ ID NO. 3/4: show the nucleotide and amino acid sequence of wt-streptavidin in the region of amino acids 44–47, SEQ ID NO. 5/6: show the nucleotide and amino acid sequence of the streptavidin mutein 1 in the region of amino acids 44–47, SEQ ID NO. 7/8: show the nucleotide and amino acid sequence of the streptavidin mutein 2 in the region of amino acids 44–47, SEQ ID NO. 9: shows the nucleotide sequence of the oligonucleotide primer P1, SEQ ID NO. 10: shows the nucleotide sequence of the oligonucleotide primer P2, SEQ ID NO. 11: shows the nucleotide sequence of the oligonucleotide primer P3, SEQ ID NO. 12: shows the nucleotide sequence of the oligonucleotide primer P4, SEQ ID NO. 13: shows the nucleotide sequence of the oligonucleotide primer P5, SEQ ID NO. 14: shows the nucleotide sequence of the oligonucleotide primer P6 and SEQ ID NO. 15: shows the nucleotide sequence of the oligonucleotide primer P7.

SEQ ID NO. 16: shows a general formula for muteins described herein.

SEQ ID NO: 17 shows the wild type sequence of streptavidin.

EXAMPLES

General methods

DNA manipulations were carried out by conventional genetic engineering methods (see e.g. Sambrook et al., Molecular Cloning. A Laboratory Manual (1989), Cold Spring Harbor Press). In general the E. coli K12 strain JM83 (Yanisch-Peron et al., (1985), Gene 33, 103–119) was used for cloning and expression with the exception of the expression under the control of the T7 promoter which was carried out according to Schmidt and Skerra (1994), supra. Sequencings were carried out by plasmid sequencing according to the standard dideoxy technique using the T7 sequencing kit from Pharmacia, Freiburg. The primers and oligonucleotides were synthesized using an Applied Biosystems DNA synthesizer.

Example 1

Preparation of an expression bank for streptavidin muteins

In order to construct the vector pASK75-SAp which carries the gene sequence coding for a minimal streptavidin fused to the coding sequence of the OmpA signal peptide (cf. FIG. 1), the sequence coding for minimal streptavidin was amplified by PCR from the expression vector pSA1 (Schmidt and Skerra, (1994), supra) using the primers P1 and P2:

P1: 5'-GAG ATA CAG CTG CAG AAG CAG GTA TCA CCG GCA C (SEQ ID NO. 9) and

P2: 5'-CGG ATC AAG CTT ATT AGG AGG CGG CGG ACG GCT TCA C (SEQ ID NO. 10)

and Taq DNA polymerase, the reaction product was purified by gel electrophoresis, cleaved with PvuII and HindIII and ligated into the vector fragment of pASK75 cleaved with StuI and HindIII. The complete nucleotide sequence of pASK75 is stated in DE-A-44 17 598.1. The vector generated in this manner pASK75-SAp contains a DNA sequence which codes for the OmpA signal peptide fused to minimal streptavidin beginning at Ala[13].

A plasmid bank with DNA sequences which code for streptavidin derivatives mutagenized in the region of amino acid positions 44 to 47 (with reference to wt-streptavidin) was prepared by PCR amplification of pASK75-SAp using the following primers P3 and P4:

P3: 5'-TCG TGA CCG CGG GTG CAG ACG GAG CTC TGA CCG GTA CCT ACN N(C/G)N N(G/T)N N(C/G)N N(G/T)G GCA ACG CCG AGA GCC GCT AC (SEQ ID NO. 11) and

P4: 5'-CGG ATC AAG CTT ATT AGG AGG CGG CGG ACG GCT TCA C (SEQ ID NO. 12).

DNA sequences were generated in this manner which contained 32-fold degenerated codons for each of all the 20 amino acids or a stop codon at each of the four positions 44 to 47. In addition a KpnI restriction site was generated at the site in the region of the codons for the amino acids 41/42. The resulting PCR products were purified by gel electrophoresis, cleaved with SacII and HindIII and ligated into the correspondingly cleaved vector fragment of pASK75-SAp.

E. coli JM83 cells were transformed with the vector mixture using the calcium chloride method (Sambrook et al., 1989).

Example 2
Identification of streptavidin muteins with an increased binding affinity for peptide ligands In order to identify streptavidin muteins with an increased binding affinity for peptide ligands, a fusion protein was prepared comprising the alkaline phosphatase of E. coli (PhoA) and the strep-tag II peptide (WSHPQFEK) which was attached to its C-terminus. For this the complete phoA gene including its own signal sequence and translation initiation region was amplified by PCR according to a method published by Skerra (Nucleic Acids Res. 20 (1992), 3551 to 3554) from chromosomal E. coli K12 W3110 DNA (Bachmann, Bacteriol. Rev. 36 (1972), 525–557) using the phosphorothioate primers P5 and P6 and pfu DNA polymerase:

P5: 5'-TAA TGT TCT AGA ACA TGG AGA AAA TAA AGT GAA ACA AAG GAC (SEQ ID NO. 13) and

P6: 5'-GCT AGG CGG TTT CAG CCC CAG AGC GGC TTT C (SEQ ID NO: 14).

The PCR product obtained in this manner was purified and cleaved with the restriction enzyme XbaI. This DNA fragment was then inserted in several steps into the plasmid pASK75-strepII (constructed from pASK75 by site-specific mutagenesis using the oligodeoxynucleotide P7 5'-CAC AGG TCA AGC TTA TTA TTT TTC GAA CTG CGG GTG AGA CCA AGC GCT GCC TGC (SEQ ID NO. 15) while replacing the region between XbaI and Eco47III to obtain the expression plasmid pASK75-PhoA strep II.

The protein production took place in 2 l LB medium containing 100 μg/ml ampicillin in which the gene expression was induced at $A_{550}=0.5$ by addition of 0.2 μg/ml anhydrotetracyclin. The induction was carried out overnight at a temperature of 37° C. The PhoA/strep-tag II fusion enzyme was then purified from the periplasmic cell fraction by streptavidin affinity chromatography using diaminobiotin as the eluting agent according to the procedure of Schmidt and Skerra (1994), supra. Due to the presence of Zn(II) ions and Mg(II) ions in the active centre of the enzyme the chromatography buffer contained no EDTA.

The plasmid bank obtained in example 1 was plated out on a hydrophilic GVWP membrane (Millipore, Eschborn) which had been placed on an Agar plate containing LB medium which contained 100 μg/ml ampicillin. The membrane was incubated for 7 to 8 hours at 37° C. until colonies became visible.

Then a second membrane was prepared, an Immobilon-P membrane (Millipore, Eschborn) which was coated for ca. 6 hours with anti-streptavidin immunoglobulin (Sigma, Deisenhofen) at a concentration of 720 μg/ml in PBS (4 mM $KH_2PO_4$, 16 mM $Na_2HPO_4$, 115 mM NaCl) and afterwards was blocked for ca. 2 hours in 3% w/v bovine serum albumin (BSA), 0.5% v/v Tween in PBS.

This second membrane was placed on a M9 minimal agar plate which contained 100 μg/ml ampicillin and 0.2 μg/ml anhydrotetracyclin. Subsequently the GVWP membrane with the colonies on the upper side was placed on the second membrane and the relative positions of the two membranes was marked. After incubation overnight at room temperature the upper membrane with the colonies was removed and stored on a fresh LB ampicillin agar plate at 4° C. The second membrane was also removed from the agar plate and washed three times for 1 minute while shaking in PBS/Tween (0.1% v/v Tween in PBS). Subsequently the membrane was admixed with 10 ml fresh PBS/Tween solution containing the purified PhoA/strep-tagII fusion protein (ca. 1–2 μg/ml). After incubating for one hour at room temperature it was washed again twice in PBS/Tween and twice in PBS buffer. The signal generation took place for 1 to 2 hours in the presence of 10 ml AP buffer (100 mM Tris, pH 8.8, 100 mM NaCl, 5 MM $MgCl_2$) with addition of 30 μl bromo-chloro-indolylphosphate (BCIP) (50 mg/ml in dimethylformamide) and 5 μl nitroblue tetrazolium (NBT) (75 mg/ml in 70% v/v dimethylformamide). The colour spots which formed in this process were assigned to corresponding colonies on the first membrane. After isolation and culture of these clones, two streptavidin muteins "1" and "2" were identified. The nucleotide and amino acid sequences in the mutagenized region for wt-streptavidin and for the muteins were as follows:

| wt-streptavidin | GAG | TCG | GCC | GTC | (SEQ ID NO. 3) |
|---|---|---|---|---|---|
| | Glu[44] | Ser[45] | Ala[46] | Val[47] | (SEQ ID NO. 4) |
| mutein "1" | GTC | ACG | GCG | CGT | (SEQ ID NO. 5) |
| | Val | Thr | Ala | Arg | (SEQ ID NO. 6) |
| mutein "2" | ATC | GGT | GCG | AGG | (SEQ ID NO. 7) |
| | Ile | Gly | Ala | Arg | (SEQ ID NO. 8) |

Example 3
Production of streptavidin muteins on a preparative scale

The known expression system for recombinant minimal streptavidin (Schmidt and Skerra (1994), supra) was used to produce streptavidin muteins on a preparative scale. For this the major part of the coding region was removed from the vector pSA1 which contains the coding region of wt-streptavidin and the T7 promoter by using the singular SacII and HindIII restriction sites and replaced by the corresponding regions from the mutated pASK75-SAp plasmids. wt-streptavidin and the streptavidin muteins were subsequently expressed in the form of cytoplasmic inclusion bodies, solubilized, renatured and purified by fractional ammonium sulphate precipitation as described by Schmidt and Skerra (1994) supra. The purity of the proteins was checked by SDS-PAGE using the discontinuous buffer system of Fling and Gregerson (Anal. Biochem. 155 (1986), 83–88). Characterization of the purified proteins that were dialysed against water by electrospray ionisation mass spectrometry yielded masses of 13334 for the recombinant wt-streptavidin (theoretical 13331.5), 13371 for mutein "1" (theoretical 13372.6) and 13344 for mutein "2" (theoretical 13342.5).

Example 4

Affinity chromatography

The streptavidin muteins prepared in example 3 and wt-streptavidin were coupled to NHS-activated Sepharose 4B (Pharmacia Freiburg) at a loading of 5 mg protein per ml swollen gel (Schmidt and Skerra, 1994, supra). After blocking the remaining active groups overnight with 100 mM Tris/HCl, pH 8.0, 2 ml of the gel was placed in a column with a diameter of 7 mm. In order to examine the behaviour of the streptavidin muteins immobilized in this manner in the affinity purification of strep-tag or strep-tagII-carrying fusion proteins, the recombinant protease inhibitor cystatin (Schmidt and Skerra 1994, supra) which was either fused to strep-tag or strep-tagII as well as the PhoA/strep-tagII fusion protein mentioned above were used. The fusion proteins were produced in an expression system by secretion into the periplasmic space and the periplasmic cell fraction was prepared as described in Schmidt & Skerra (1994), supra.

The chromatography was carried out in the presence of 100 mM Tris/HCl, pH 8.0 containing 1 mM EDTA (except in the case of PhoA) at a flow rate of ca. 20 ml/h and the eluate absorbance was measured at 280 nm. After applying a sample of 10 ml corresponding to the periplasmic cell fraction of 1 l $E.$ $coli$ culture medium, the column was washed until the absorbance at 280 nm had reached the base line. Afterwards bound protein was eluted step-wise by applying 10 ml each of diaminobiotin, desthio-biotin and biotin (all from Sigma, Deisenhofen) at a concentration of 2.5 mM in chromatography buffer and in the stated order.

It turned out that, in contrast to wt-streptavidin, the use of diaminobiotin did not lead to an elution in the case of the streptavidin muteins. When the biotin derivative desthiobiotin, which binds with a higher affinity to streptavidin, was used an elution with a sharp maximum was also achieved in the case of the muteins. This was quantitative since in the subsequent elution with biotin essentially no amounts of fusion protein could be detected in the eluate (cf. FIG. 4).

Example 5

ELISA

An ELISA was carried out to determine the binding affinity of the streptavidin muteins for the peptide ligand strep-tagII.

The wells of a 96-well microtitre plate (Becton Dickinson Co., Oxnard, Calif.) were coated overnight with 100 µl of a solution of recombinant wt-streptavidin or the muteins "1" or "2" at a concentration in each case of 100 µg/ml in 50 mM NaHCO$_3$, pH 9.6. The wells were then blocked for 2.5 hours with 3% w/v BSA, 0.5% v/v Tween in PBS. After washing three times with PBS/Tween, 50 µl of the same buffer was added to each well. 20 µl from a solution of 20 µl of 4.85 µM purified and dialysed PhoA/strep-tag II fusion protein plus 30 µl PBS/Tween was added to the first well of each row and mixed. A dilution series was set up in the other wells of a row by pipetting 50 µl (from a total of 100 µl) out of the first well and mixing it with the contents (50 µl) of the next well in the same row etc. In this manner concentrations of the fusion protein between 970 nM in the first well of each row and 0.19 nM in the tenth well were obtained.

After incubating for one hour the solutions were removed and the wells were each washed twice with PBS/Tween and with PBS. Subsequently 100 µl of a solution of 0.5 mg/ml p-nitrophenyl phosphate in 1 mM ZnSO$_4$, 5 mM MgCl$_2$, 1 mM Tris/HCl, pH 8.0 was pipetted into each well. The activity of the bound fusion protein was measured using a SpectraMAX 250 photometer (Molecular Devices, Sunnyvale, Calif.) as an absorbance change at 410 nm per time.

The data were evaluated assuming a single binding equilibrium between streptavidin (mutein) monomers (P) and the PhoA/strep-tag II fusion protein (L) which yielded a dissociation constant $K_D=[P][L]/[P\cdot L]$. Under the condition that $[P]_{TOT}=[P]+[P\cdot L]$ and that [L] is very much larger than [P·L] so that $[L]_{TOT}$ is approximately the same as $[L][P\cdot L]=[L]_{TOT}$ $[P]_{TOT}/(K_D+[L]_{TOT})$ applies for the amount of bound fusion protein. FIG. 2 shows a graph of the experimental results obtained.

It can be seen from the binding curves that the two streptavidin muteins have a very similar affinity for the strep-tap II fusion protein which is more than an order of magnitude higher than the affinity of wt-streptavidin.

Example 6

Fluorescence titration

In order to determine the dissociation constant of the 1:1 complex of the streptavidin muteins (considered as a monomer) and the peptide ligands, a fluorescence titration was carried out with the strep-tag II synthesized by peptide chemistry.

The peptide with the sequence Abz-Trp-Ser-His-Pro-Gln-Phe-Glu-Lys-COOH (SEQ ID NO: 6, with N-terminal Abz added thereto) (Abz represents o-aminobenzoic acid i.e. anthranilic acid) was synthesized stepwise on a solid phase from Fmoc-protected amino acids according to methods known to a person skilled in the art in the order C-terminus to N-terminus wherein Abz was coupled in the last step as a Boc-protected derivative. The peptide was subsequently cleaved from the carrier and freed of the protecting groups. After purification by HPLC the mole mass was confirmed by means of field desorption mass spectrometry.

The fluorescence titration was carried out with an LS50 fluorescence spectrophotometer from the Perkin Elmer Company (Langen) in a 1·1 cm$^2$ quartz cuvette which was thermostated at 25° C. The wavelengths for excitation and emission were 280 nm and 340 nm respectively with a respective slit width of 5 nm. 2 ml of the solution of wt-streptavidin or the muteins "1" and "2", which were prepared as described in example 3 and had been dialysed against 1 mM EDTA, 100 mM Tris/HCl pH 8.0, were placed in the cuvette at a concentration of 1 µM (determined by absorbance photometry for the respective monomer using an extinction coefficient of $\epsilon_{280}$=40455 M$^{-1}$ cm$^{-1}$). Then volumes of 1 µl or 4 µl of a 0.5 mM solution of the peptide in the same buffer were repeatedly added by pipette (a total of 40 µl) and after mixing with a stirring bar the fluorescence intensity was read. The data were evaluated as described in FIG. 3.

SEQUENCE LISTING

<160> NUMBER OF SEQ ID NOS: 17

<210> SEQ ID NO 1
<211> LENGTH: 9
<212> TYPE: PRT
<213> ORGANISM: Artificial sequence
<220> FEATURE:
<221> NAME/KEY: BINDING
<223> OTHER INFORMATION: Binding ligand for streptavidin

<400> SEQUENCE: 1

Ala Trp Arg His Pro Gln Phe Gly Gly
 1               5

<210> SEQ ID NO 2
<211> LENGTH: 8
<212> TYPE: PRT
<213> ORGANISM: Artificial sequence
<220> FEATURE:
<221> NAME/KEY: BINDING
<223> OTHER INFORMATION: Binding ligand for streptavidin

<400> SEQUENCE: 2

Trp Ser His Pro Gln Phe Glu Lys
 1               5

<210> SEQ ID NO 3
<211> LENGTH: 12
<212> TYPE: DNA
<213> ORGANISM: Artificial sequence
<220> FEATURE:
<221> NAME/KEY: CDS
<223> OTHER INFORMATION: Synthesized

<400> SEQUENCE: 3 gagtcg gccg tc                                                      12

<210> SEQ ID NO 4
<211> LENGTH: 4
<212> TYPE: PRT
<213> ORGANISM: Streptomyces avidinii
<220> FEATURE:
<223> OTHER INFORMATION: Amino acids 44-47 of wild type streptavidin

<400> SEQUENCE: 4

Glu Ser Ala Val

<210> SEQ ID NO 5
<211> LENGTH: 12
<212> TYPE: DNA
<213> ORGANISM: Artificial sequence
<220> FEATURE:
<221> NAME/KEY: CDS
<223> OTHER INFORMATION: Synthesized

<400> SEQUENCE: 5
gtcacggcgc gt                                                       12

<210> SEQ ID NO 6
<211> LENGTH: 4
<212> TYPE: PRT
<213> ORGANISM: Artificial sequence
<220> FEATURE:
<221> NAME/KEY: MUTAGEN
<223> OTHER INFORMATION: Mutagen of amino acids 44-47 of wild type
      streptavidin

<400> SEQUENCE: 6

Val Thr Ala Arg

<210> SEQ ID NO 7
<211> LENGTH: 12
<212> TYPE: DNA
<213> ORGANISM: Artificial sequence
<220> FEATURE:
<221> NAME/KEY: CDS
<223> OTHER INFORMATION: Synthesized

<400> SEQUENCE: 7
atcggtgcga gg                                                          12

<210> SEQ ID NO 8
<211> LENGTH: 4
<212> TYPE: PRT
<213> ORGANISM: Artificial sequence
<220> FEATURE:
<221> NAME/KEY: MUTAGEN
<223> OTHER INFORMATION: Mutagen of amino acids 44-47 of wild type
      streptavidin

<400> SEQUENCE: 8

Ile Gly Ala Arg

<210> SEQ ID NO 9
<211> LENGTH: 34
<212> TYPE: DNA
<213> ORGANISM: Artificial sequence
<220> FEATURE:
<221> NAME/KEY: primer_bind
<223> OTHER INFORMATION: primer for sequence encoding streptavidin

<400> SEQUENCE: 9
gagatacagc tgcagaagca ggtatcaccg gcac                                  34

<210> SEQ ID NO 10
<211> LENGTH: 37
<212> TYPE: DNA
<213> ORGANISM: Artificial sequence
<220> FEATURE:
<221> NAME/KEY: primer_bind
<223> OTHER INFORMATION: primer for sequence encoding streptavidin

<400> SEQUENCE: 10
cggatcaagc ttattaggag cgggcggacg gcttcag                               37

<210> SEQ ID NO 11
<211> LENGTH: 74
<212> TYPE: DNA
<213> ORGANISM: Artificial sequence
<220> FEATURE:
<221> NAME/KEY: primer_bind
<223> OTHER INFORMATION: degenerate primer sequence for use in encoding
      mutations in
<223> OTHER INFORMATION: amino acids 44-47 of streptavidin. "n" is used
      at positions
<223> OTHER INFORMATION: 42,43,45,46,48,49,51 and 52. In each case, "n"
      can be a, c,
<223> OTHER INFORMATION: t, or g.

<400> SEQUENCE: 11
tcgtgaccgc gggtgcagac ggagctctga ccggtaccta cnnsnnknns nnkggcaacg      60
ccgagagccg ctag                                                        74

```
<210> SEQ ID NO 12
<211> LENGTH: 37
<212> TYPE: DNA
<213> ORGANISM: Artificial sequence
<220> FEATURE:
<221> NAME/KEY: primer_bind
<223> OTHER INFORMATION: Primer sequence used in connection with SEQ ID
      NO: 12 to
<223> OTHER INFORMATION: generate mutations of streptavidin

<400> SEQUENCE: 12
cggatcaagc ttattaggag cgggcggagc gcttcac                              37

<210> SEQ ID NO 13
<211> LENGTH: 42
<212> TYPE: DNA
<213> ORGANISM: Artificial sequence
<220> FEATURE -continued
<210> SEQ ID NO 17
<211> LENGTH: 159
<212> TYPE: PRT
<213> ORGANISM: Streptomyces avidinii

<400> SEQUENCE: 17

Asp Pro Ser Lys Asp Ser Lys Ala Gln Val Ser Ala Ala Glu Ala Gly
 1               5                  10                  15

Ile Thr Gly Thr Trp Tyr Asn Gln Leu Gly Ser Thr Phe Ile Val Thr
             20                  25                  30

Ala Gly Ala Asp Gly Ala Leu Thr Gly Thr Tyr Glu Ser Ala Val Gly
         35                  40                  45

Asn Ala Glu Ser Arg Tyr Val Leu Thr Gly Arg Tyr Asp Ser Ala Pro
     50                  55                  60

Ala Thr Asp Gly Ser Gly Thr Ala Leu Gly Trp Thr Val Ala Trp Lys
 65                  70                  75                  80

Asn Asn Tyr Arg Asn Ala His Ser Ala Thr Thr Trp Ser Gly Gln Tyr
                 85                  90                  95

Val Gly Gly Ala Glu Ala Arg Ile Asn Thr Gln Trp Leu Leu Thr Ser
             100                 105                 110

Gly Thr Thr Glu Ala Asn Ala Trp Lys Ser Thr Leu Val Gly His Asp
             115                 120                 125

Thr Phe Thr Lys Val Lys Pro Ser Ala Ala Ser Ile Asp Ala Ala Lys
         130                 135                 140

Lys Ala Gly Val Asn Asn Gly Asn Pro Leu Asp Ala Val Gln Gln
145                 150                 155

We claim:

1. Polypeptide, selected from muteins of streptavidin, wherein it (a) contains at least one mutation in the region of the amino acid positions 44 to 53 with reference to the amino acid sequence of wild type streptavidin as set forth at SEQ ID NO: 17 and (b) has a higher binding affinity than wild type-streptavidin for peptide ligands comprising the amino acid sequence Trp Xaa His Pro Gln Phe Xaa Xaa (SEQ ID NO: 16) in which Xaa between Trp and His represents an arbitrary amino acid and the two C terminal Xaa residues either both denote Gly or the first denotes Glu and the second denotes Arg or Lys.

2. Polypeptide as claimed in claim 1, wherein
it is the mutein of a minimal streptavidin which begins N-terminally in the region of the amino acids 10 to 16 of wild type streptavidin and terminates C-terminally in the region of the amino acids 133–142 of wild type streptavidin.

3. Polypeptide as claimed in claim 1, wherein
at least one mutation is present in the region of amino acid positions 44 to 47.

4. Polypeptide as claimed in claim 1, wherein
Glu is replaced by a hydrophobic aliphatic amino acid at position 44, an arbitrary amino acid is present at position 45, a hydrophobic aliphatic amino acid is present at position 46 or/and Val is replaced by a basic amino acid at position 47.

5. Polypeptide as claimed in claim 4, wherein
Ala is present at position 46.

6. Polypeptide as claimed in claim 4, wherein
Arg is present at position 47.

7. Polypeptide as claimed in claim 6, wherein
the sequence $Val^{44}$-$Thr^{45}$-$Ala^{46}$-$Arg^{47}$ (SEQ ID NO: 6) is present in the region of amino acid positions 44 to 47.

8. Polypeptide as claimed in claim 6, wherein
the sequence $Ile^{44}$-$Gly^{45}$-$Ala^{46}$-$Arg^{47}$ (SEQ ID NO: 8) is present in the region of amino acid positions 44 to 47.

9. Polypeptide as claimed in one of the claim 1, wherein
the binding affinity for the peptide ligand is such that a competitive elution can take place by streptavidin ligands selected from biotin, iminobiotin, lipoic acid, desthiobiotin, diaminobiotin, HABA or/and dimethyl-HABA.

10. Polypeptide as claimed in claim 1, wherein the affinity constant of the complex of polypeptide and peptide ligand is $>2.7 \times 10^4$ $M^{-1}$ with respect to Ala Trp Arg His Pro Gln Phe Gly Gly (SEQ ID NO: 1 ), and $>1.4 \times 10^4 M^{-1}$ with respect to Trp Ser His Pro Gln Phe Glu Lys (SEQ ID NO: 2).

11. Polypeptide as claimed in one of the claim 1, wherein
it carries at least one labelling group.

12. Nucleic acid, wherein it comprises a sequence coding for a streptavidin mutein as claimed in claim 1.

13. Vector comprising at least one copy of a nucleic acid as claimed in claim 12 in an operatively functionally environment.

14. Cell, wherein it is transformed or transfected with a vector as claimed in claim 13.

15. Process for the production of a streptavidin mutein as claimed in claim 1, characterized by the following steps:

(a) transforming a suitable host cell with a vector which contains a nucleic acid coding for the streptavidin mutein, (b) culturing the host cell under conditions in which an expression of the streptavidin mutein takes place, (c) isolating the polypeptide.

16. Method as claimed in claim 15, wherein step (c) comprises lysing the host cells, isolating the streptavidin mutein in the form of inclusion bodies and renaturing the streptavidin mutein.

17. Method as claimed in claim 15, wherein the expression in step (b) comprises the expression of a signal peptide-carrying streptavidin and its secretion into the periplasma of the host cell or the culture medium.

18. Method as claimed in claim 15, wherein the host cell is *E. coli*.

19. A method for the isolation, purification or determination of a protein that is fused with a peptide sequence of the formula Trp-Xaa-His-Pro-Gln-Phe-Xaa-Xaa (SEQ ID NO: 16) in which Xaa between Trp and His represents an arbitrary amino acid and the two terminal Xaas either both denote Gly or the first Xaa denotes Glu and the second Xaa denotes Arg or Lys, comprising contacting a liquid containing the protein with a polypeptide streptavidin mutein of claim 1, under suitable conditions to bind the peptide sequence to the streptavidin mutein, and separating resulting complex from said liquid.

20. The method as claimed in claim 19, wherein the streptavidin mutein is bound to a solid phase or is capable of binding thereto.

21. The method as claimed in claim 19, wherein in order to release the fusion protein from the complex the complex is incubated with an adequate amount of a ligand for the streptavidin mutein selected from biotin and derivatives thereof.

22. The method as claimed in claim 21, wherein the biotin derivative is desthiobiotin.

23. The method as claimed claim 19, wherein the peptide sequence is selected from AWRHPQFGG or WSHPQFEK.

24. The method of claim 19, further comprising releasing said protein from said complex.

25. The method of claim 19, further comprising determining said protein.

26. A method for determination of a protein which is fused with a peptide sequence of formula Trp-Xaa-His-Pro-Gln-Phe-Xaa-Xaa (SEQ ID NO: 16), in which Xaa between Trp and His represents an arbitrary amino acid and the two terminal Xaa either both represent Gly or non-terminal Xaa denotes Glu and terminal Xaa denotes Arg or Lys, comprising contacting said protein with the streptavidin mutein of claim 11 under suitable conditions in order to bind the streptavidin mutein, and determining the label.

27. The method of claim 26, wherein said peptide sequence is Ala Trp Arg His ProGln Phe Gly Gly (SEQ ID NO: 1) or Trp Ser His Pro Gln Phe Glu Lys (SEQ ID NO. 2).

28. A method for immobilizing protein which is fused with a peptide sequence of formula Trp-Xaa-His-Pro-Gln-Phe-Xaa-Xaa (SEQ ID NO: 16) in which Xaa between Trp and His represents an arbitrary amino acid and the two terminal Xaas either both denote Gly or non-terminal Xaa denotes Glu and terminal Xaa denotes Arg or Lys, comprising contacting said protein to a solid phase which carries the peptide of claim 1, under conditions for immobilizing said protein.

29. A method for determination or isolation of substances which carry a group capable of binding to streptavidin, comprising contacting said substances with the streptavidin mutein of claim 1 under suitable conditions for binding thereto, and determining or isolating said substance.

30. Reagent kit comprising the streptavidin mutein of claim 1, and at least one conventional buffer, auxiliary substance, or additive.

* * * * *

UNITED STATES PATENT AND TRADEMARK OFFICE
CERTIFICATE OF CORRECTION

PATENT NO. : 6,103,493
DATED : Aug. 15, 2000
INVENTOR(S) : Skerra et al

It is certified that error appears in the above-identified patent and that said Letters Patent is hereby corrected as shown below:

In the cover page, insert -- Foreign Application Priority Data
Oct. 10, 1996     Germany     196 41 876.3 --.

column 1, line 19, change "1013" to -- $10^{13}$ --.
column 2, line 59, change "t he" to -- the --.
column 10, line 34, change "MM" to -- mM --.

Signed and Sealed this

First Day of May, 2001

Attest:

NICHOLAS P. GODICI

Attesting Officer     Acting Director of the United States Patent and Trademark Office